US006561970B1

(12) United States Patent
Carpentier et al.

(10) Patent No.: US 6,561,970 B1
(45) Date of Patent: *May 13, 2003

(54) METHODS FOR TREATING IMPLANTABLE BIOLOGICAL TISSUES TO MITIGATE THE CALCIFICATION THEREOF AND BIOPROSTHETIC ARTICLES TREATED BY SUCH METHODS

(75) Inventors: Sophie M. Carpentier, Paris (FR); Alain F. Carpentier, Paris (FR)

(73) Assignee: Edwards Lifesciences Corporation, Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 338 days.

(21) Appl. No.: 08/764,821

(22) Filed: Dec. 12, 1996

Related U.S. Application Data

(62) Division of application No. 08/282,358, filed on Jul. 29, 1994, now abandoned.

(51) Int. Cl.$^7$ .................................................. A61F 2/04
(52) U.S. Cl. ....................... 600/36; 623/915; 623/23.72; 623/2.13; 8/94.11
(58) Field of Search ............................. 8/94.1 R, 94.11, 8/94.15, 94.2; 623/2, 11, 2.13, 915, 23.72; 600/36

(56) References Cited

U.S. PATENT DOCUMENTS

| 2,393,580 A | 1/1946 | Weiskopf |
| 3,093,439 A | 6/1963 | Bothwell ..................... 8/94.11 |
| 3,961,097 A | 6/1976 | Gravlee, Jr. |

(List continued on next page.)

FOREIGN PATENT DOCUMENTS

| DE | 1 063 330 | 10/1956 |
| EP | 0 347 496 A1 | 11/1988 |
| WO | WO 93/19209 | 9/1993 |
| WO | 95/11047 | 4/1995 |

OTHER PUBLICATIONS

Abstracts of patent Nos. EP 52288, EP 347496, WO84 01879, WO 84 01894, WO8906945, EP065827, EP 0103946, and EP 0103947.*
Abstract of Russian patent SU1651890 published May 23, 1991.*
"Separation of glutaraldehyde and some of its aldol condensation products by hydroxylaldehyde group affinity chromatography", L. Holmquist, M. Lewin, *Biochem. Bioph. Meth*, vol. 22 (1991) pp 321–329.
"The impurities in commercial glutaraldehyde and their effect on the fixation of brain", E. A. Robertson, R. L. Schultz, *J. Ultrastructure Research*, vol. 30 (1970) pp 275–287.

(List continued on next page.)

*Primary Examiner*—Paul Prebilic
(74) *Attorney, Agent, or Firm*—Debra D. Condino; John Christopher James; Guy L. Cumberbatch

(57) ABSTRACT

A method for treating fixed biological tissue inhibits calcification of the biological tissue following implantation thereof in a mammalian body. The method includes placing the biological tissue in contact with glutaraldehyde and then heating the glutaraldehyde. Alternatively, methods other than heating (e.g., chemical or mechanical means), for effecting polymerization of the glutaraldehyde may also be utilized. Alternatively, the tissue may be heat treated prior to fixing thereof. Alternatively, methods other than glutaraldehyde may also be used for fixing the tissue. The biological tissue may be so treated at any time prior to implantation thereof in a mammalian body.

29 Claims, 2 Drawing Sheets

U.S. PATENT DOCUMENTS

| | | | |
|---|---|---|---|
| 4,050,893 A | | 9/1977 | Hancock et al. ............. 8/94.11 |
| 4,082,507 A | | 4/1978 | Sawyer ........................ 8/94.11 |
| 4,120,649 A | | 10/1978 | Schechter .................... 8/94.11 |
| 4,239,492 A | | 12/1980 | Holman et al. ............. 8/94.11 |
| 4,323,358 A | | 4/1982 | Lentz et al. |
| 4,350,492 A | | 9/1982 | Wright et al. |
| 4,378,224 A | * | 3/1983 | Nimni et al. ................ 8/94.11 |
| 4,402,697 A | | 9/1983 | Pollock et al. .................... 8/94 |
| 4,405,327 A | | 9/1983 | Pollock |
| 4,597,762 A | | 7/1986 | Walter et al. |
| 4,648,881 A | | 3/1987 | Carpentier et al. ........... 623/11 |
| 4,770,665 A | | 9/1988 | Nashef ............................ 8/94 |
| 4,786,287 A | | 11/1988 | Nashef et al. ............... 8/94.11 |
| 4,798,611 A | * | 1/1989 | Freeman, Jr. ................ 8/94.1 |
| 4,885,005 A | | 12/1989 | Nashef et al. ............... 8/94.11 |
| 4,976,733 A | | 12/1990 | Girardot ...................... 623/11 |
| 5,002,566 A | | 3/1991 | Carpentier et al. ............ 623/2 |
| 5,068,086 A | | 11/1991 | Sklenak et al. |
| 5,104,405 A | | 4/1992 | Nimni |
| 5,595,571 A | | 1/1997 | Jaffe et al. |
| 5,632,778 A | | 5/1997 | Goldstein |
| 5,674,298 A | * | 10/1997 | Levy et al. .................. 8/94.11 |

OTHER PUBLICATIONS

"Weighing the choices in radiation sterilization: Electron–Beam and Gamma", J. Williams, *Medical Device & Diagnostic Industry,* (Mar. 1995) pp 68–72.

"Principles of Tissue Valve Transplantation", A. Carpentier, *Biological Tissue in Heart Valve Replacement,* (1972) pp 49–83.

"From Xenograft to Bioprosthesis:Evolution of concepts and Techniques of Valvular Xenografts", Carpentier et al, *Biological Tissue in Heart Valve Replacement* (1972) pp 515–541.

"Biological factors affecting long–term results of valvular heterografts", Carpenter et al, *Journal of Thoracic Cardiovascular Surgery,* vol. 58 (Jul. 1969) pp 467–483.

"Continuing improvements in valvular bioprostheses", Carpentier et al, *Journal of Thoracic Cardiovascular Surgery,* (Jan. 1982) pp 27–42.

* cited by examiner

METHODS FOR TREATING IMPLANTABLE BIOLOGICAL TISSUES TO MITIGATE THE CALCIFICATION THEREOF AND BIOPROSTHETIC ARTICLES TREATED BY SUCH METHODS

RELATED APPLICATION

This application is a division of application Ser. No. 08/282,358, filed on Jul. 29, 1994, abandoned.

FIELD OF THE INVENTION

The present invention pertains generally to biomedical materials, and more particularly to preserved biological tissues, such as porcine bioprosthetic heart valves, which are implantable in a mammalian body.

BACKGROUND OF THE INVENTION

The prior art has included numerous methods for preserving or fixing biological tissues, to enable such tissues to be subsequently implanted into mammalian bodies. Examples of the types of biological tissues which have heretofore been utilized for surgical implantation include cardiac valves, vascular tissue, skin, dura mater, pericardium, ligaments and tendons.

The term "grafting" as used herein is defined as the implanting or transplanting of any living tissue or organ (See Dorlands Illustrated Medical Dictionary, 27th Edition, W.B. Saunders Co. 1988). Biological tissues which are grafted into the body of a mammal may be xenogeneic (i.e., a xenograft) or allogeneic (i.e., an allograft).

The term "bioprosthesis" defines many types of biological tissues chemically pretreated before implantation (Carpentier—See Ionescu (editor), Biological Tissue in Heart Valve Replacement, Butterworths, 1972). As opposed to a graft, the fate of a bioprosthesis is based upon the stability of the chemically treated biological material and not upon cell viability or host cell ingrowth. Chemical pretreatment includes the "fixing" or tanning of the biological tissue. Such fixing or tanning of the tissue is accomplished by exposing the tissue to one or more chemical compounds capable of cross-linking molecules within the tissue.

Various chemical compounds have been utilized to fix or cross-link biological tissues including formaldehyde, glutaraldehyde, dialdehyde starch, hexamethylene diisocyanate and certain polyepoxy compounds.

In particular, glutaraldehyde has proven to be relatively physiologically inert and suitable for fixing various biological tissues for subsequent surgical implantation (Carpentier, A., J. Thorac. Cardiovasc. Surg. 58:467–68 (1969)). In particular, examples of the types of biological tissues which have heretofore been subjected to glutaraldehyde fixation include porcine bioprosthetic heart valves and bovine pericardial tissues.

Clinical experience has revealed that glutaraldehyde-fixed bioprosthetic tissues may tend to become calcified. Such calcification of glutaraldehyde-fixed bioprosthetic tissues has been reported to occur most predominantly in pediatric patients see, Carpentier et al. and "Continuing Improvements in Valvular Bioprostheses, J. Thorac Cardiovasc. Surg. 83:27–42, 1982. Such calcification is undesirable in that it may result in deterioration of the mechanical properties of the tissue and/or tissue failure. In view of this, surgeons have opted to implant mechanical cardio-vascular valves into pediatric patients, rather than to utilize glutaraldehyde-preserved porcine valves. However, pediatric patients who receive mechanical valve implants require long term treatment with anticoagulant medications and such anticoagulation is associated with increased risk of hemorrhage.

The mechanism by which calcification occurs in glutaraldehyde-fixed bioprosthetic tissue has not been fully elucidated. However, factors which have been thought to influence the rate of calcification include:

a) patient's age
b) existing metabolic disorders (i.e., hypercalcemia, diabetes, kidney failure . . . )
c) dietary factors
d) race
e) infection
f) parenteral calcium administration
g) dehydration
h) distortion/mechanical factors
i) inadequate coagulation therapy during initial period following surgical implantation; and
j) host tissue chemistry Various efforts have been undertaken to find ways of mitigating calcification of glutaraldehyde fixed bioprosthetic tissue. Included among these calcification mitigation techniques are the methods described in U.S. Pat. No. 4,885,005 (Nashef et al.) SURFACTANT TREATMENT OF IMPLANTABLE BIOLOGICAL TISSUE TO INHIBIT CALCIFICATION; U.S. Pat. No. 4,648,881 (Carpentier et al.) IMPLANTABLE BIOLOGICAL TISSUE AND PROCESS FOR PREPARATION THEREOF; U.S. Pat. No. 4,976,733 (Girardot) PREVENTION OF PROSTHESIS CALCIFICATION; U.S. Pat. No. 4,120,649 (Schechter) TRANSPLANTS; U.S. Pat. No. 5,002,566 (Carpentier) CALCIFICATION MITIGATION OF BIOPROSTHETIC IMPLANTS; EP 103947A2 (Pollock et al.) METHOD FOR INHIBITING MINERALIZATION OF NATURAL TISSUE DURING IMPLANTATION and WO84/01879 (Nashef et al.) SURFACTANT TREATMENT OF IMPLANTABLE BIOLOGICAL TISSUE TO INHIBIT CALCIFICATION.

There remains a need for the development of new methods for inhibiting or mitigating calcification of chemically-fixed biological tissue.

It is postulated that tissue calcification may be minimized by accelerating the polymerization of glutaraldehyde solution coming into contact with the tissue prior to implantation.

SUMMARY OF THE INVENTION

The present invention specifically addresses and alleviates the above-mentioned deficiencies associated with the prior art. More particularly, the present invention comprises a method for treating glutaraldehyde fixed biological tissue or biological tissue fixed with other chemicals so as to inhibit later calcification of the tissue following implantation of the tissue into a mammalian body. The method comprises placing the biological tissue in contact with glutaraldehyde or another chemical fixative and then heating the glutaraldehyde or other fixative and/or causing the glutaraldehyde or other fixative to be polymerized by thermal, chemical or mechanical means.

In the preferred embodiment of the present invention the biological tissue is disposed within a container containing a 0.625% solution of glutaraldehyde comprising approximately 26 ml/l glutaraldehyde (25%); approximately 4.863 g/l HEPES buffer; approximately 2.65 g/l $MgCl_2 \cdot 6H_2O$; and approximately 4.71 g/l NaCl. The balance of the solution comprises double filtered $H_2O$. Sufficient NaOH is added to adjust the pH to approximately 7.4.

The glutaraldehyde solution is heated to between approximately 35–55° C. for approximately 4–22 weeks.

The biological tissue may be heat treated any time prior to implantation thereof within a mammalian body. For example, the tissue may be treated before fixing thereof. Treatment before fixing of the biological tissue merely involves heating it in a saline solution (9 g/l NaCl) or any other physiologic solution at 25–80° C. for a few seconds to 22 weeks. Alternatively, the tissue may be treated during fixing thereof, while the tissue is disposed within a glutaraldehyde solution. Treatment during fixing of the biological tissue merely involves heating of the glutaraldehyde solution to approximately 25–80° C. for approximately a few seconds to several months. The preferred range is 35 to 55° C. for 4–22 weeks.

Alternatively, the biological tissue is treated after fixing thereof, and before storage thereof. Such treatment is preferably accomplished while the biological tissue remains within the glutaraldehyde solution utilized during the fixing process and/or is disposed with a glutaraldehyde solution within which the biological tissue is to be stored and again merely comprises heating of the glutaraldehyde solution to approximately 25–80° C. for approximately 4–22 weeks.

Alternatively, the biological tissue is treated after storage thereof, typically a short time prior to implantation within a mammalian body. The biological tissue is preferably heated within the glutaraldehyde solution within which it has been stored by merely heating the glutaraldehyde solution to approximately 35–55° C. for approximately 4–22 weeks.

Alternatively, the biological tissue is treated during an antimineralization process by adding glutaraldehyde to the antimineralization solution and heating, preferably to approximately 35–55° C. for approximately 4–22 weeks. As those skilled in the art will recognize, various antimineralization processes are utilized to inhibit mineralization of the biological tissue by calcium and various other minerals.

Heating of the glutaraldehyde appears to effect polymerization thereof. It is believed that the inhibition of calcification is due to the polymerization of glutaraldehyde contained within the biological tissue. As such, those skilled in the art will appreciate that various other cross linking agents and other processes, such as light, radiation, or chemicals, which effect polymerization of glutaraldehyde may likewise be utilized in the method for treating biological tissue of the present invention. Thus, various chemical fixatives other than glutaraldehyde and other methods for effecting polymerization of these chemicals and/or glutaraldehyde may be used alone, or in combination with heat, so as to effect polymerization of the chemicals contained within the biological tissue, thereby inhibiting later calcification of the tissue after implantation thereof in a mammalian body.

The method of inhibiting calcification of fixed biological tissue may be utilized with various different types of biological tissue such as cardiac valves, vascular tissue, skin, dura mater, pericardium, fascias, ligaments, and tendons. Those skilled in the art will realize that this list is not comprehensive in that various other types of biological tissue may also benefit from treatment thereof according to the method of the present invention.

These, as well as other advantages of the present invention will be more apparent from the following description and drawings. It is understood that changes in the specific structure shown and the described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
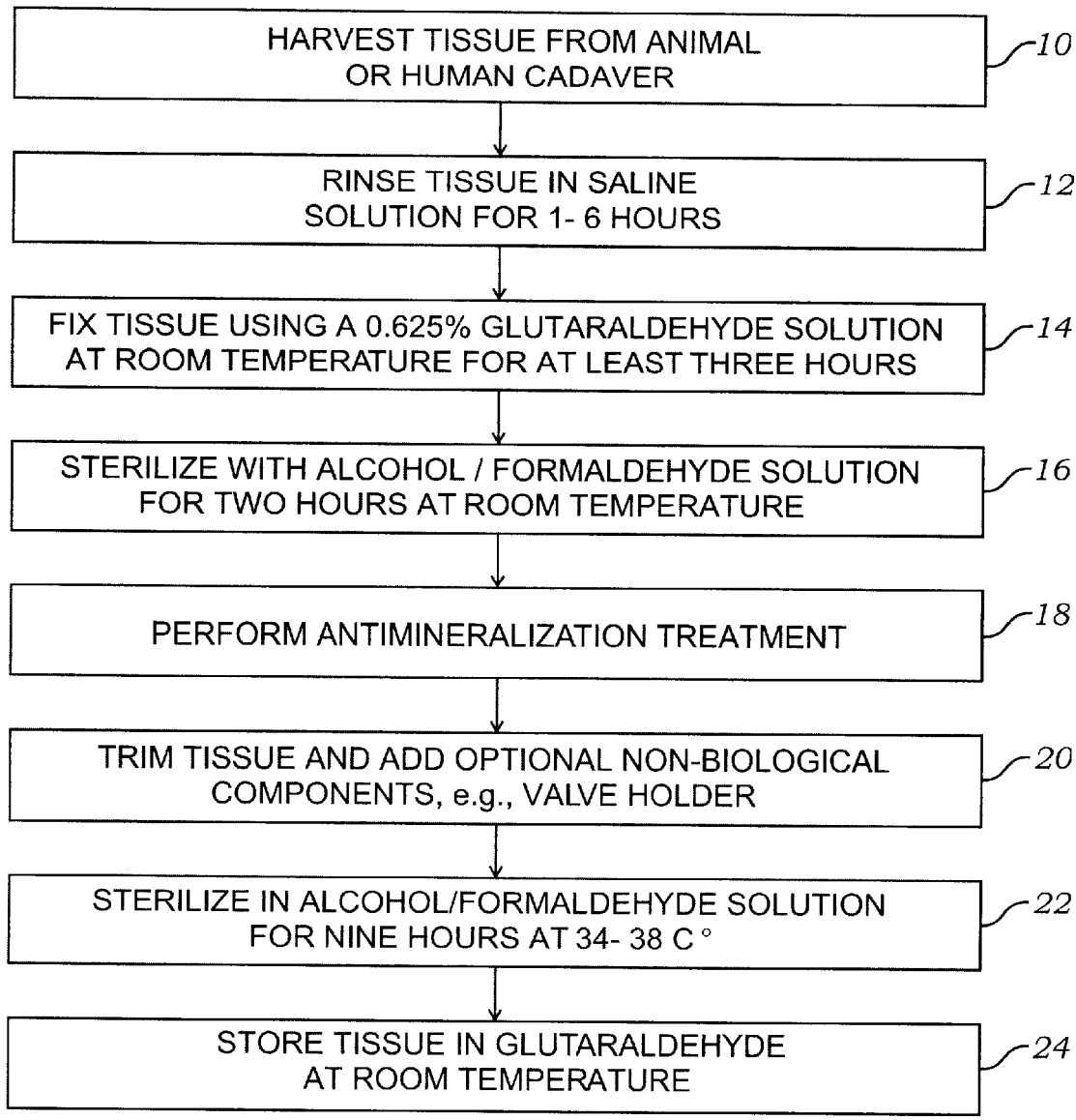
FIG. 1 is a flow diagram illustrating the prior art process for preparing biological tissue for implantation within a mammalian body comprising fixing of the biological tissue with a glutaraldehyde solution.
Figure 2:
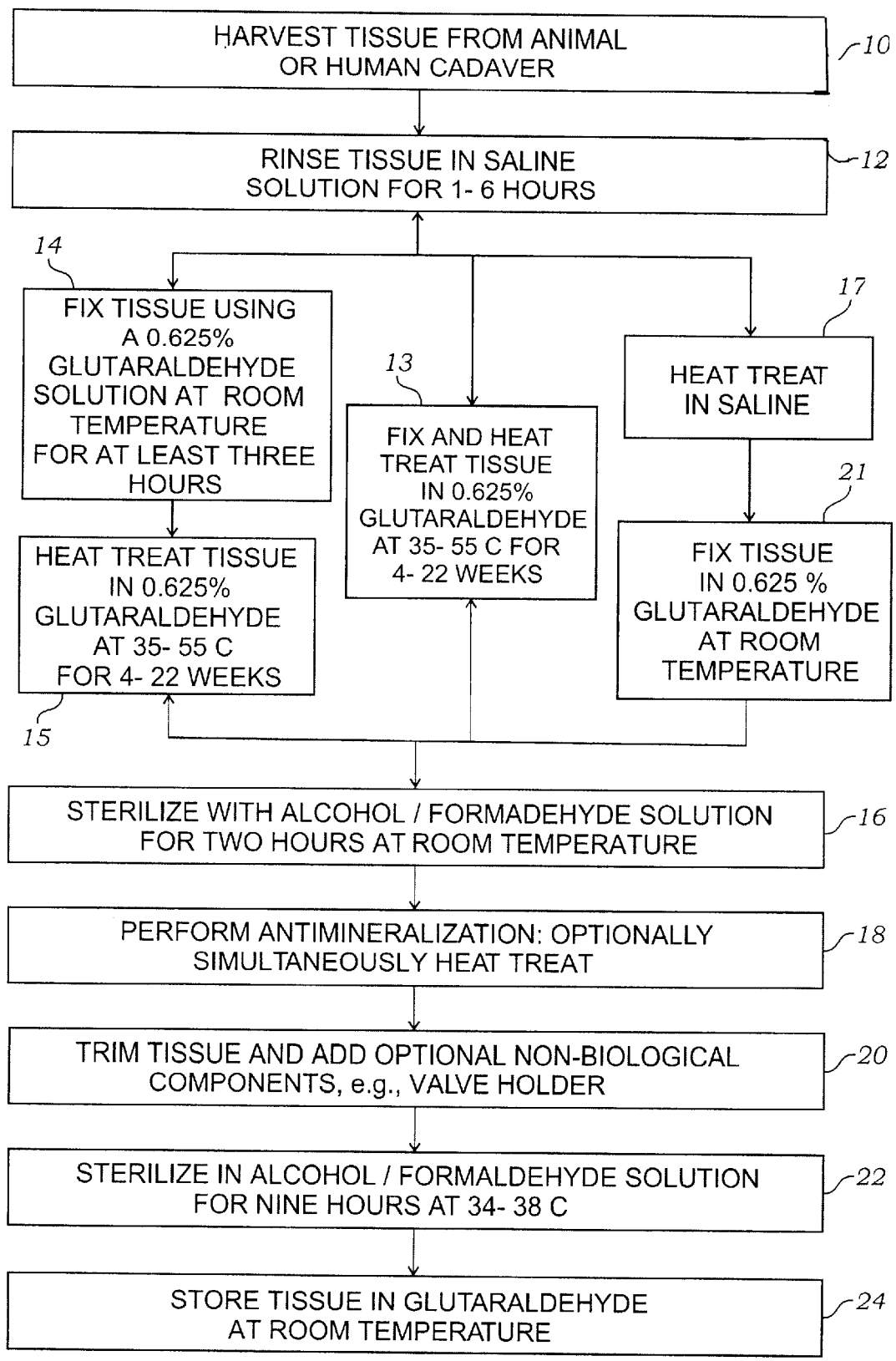
FIG. 2 is a flow chart of the preparation of biological tissue for implantation in a mammalian body comprising the method for inhibiting calcification of the biological tissue according to the present invention.

The method for treating glutaraldehyde fixed biological tissue to inhibit calcification thereof following implantation in a mammalian body is illustrated in FIG. 2 which depicts a flow chart of the presently preferred embodiment of the invention. FIG. 1 depicts a flow chart of the prior art method for preparing biological tissue for implantation within a mammalian body.

Referring now to FIG. 1, the prior art process for preparing biological tissue for implantation within a mammalian body comprises first harvesting the tissue from an animal or human cadaver (10). As those skilled in the art will recognize, various different types of tissue are routinely harvested from different animals and/or human cadavers. For example, heart valves are routinely harvested from pigs, pericardium is routinely harvested from cows or pigs, and skin is routinely harvested from human cadavers. Those skilled in the art will further recognize that new tissues are, from time to time, being found to be implantable within a mammalian body.

After harvesting, the biological tissue is rinsed in saline solution, typically for a period of 1–6 hours (12).

The tissue is next fixed using a 0.65% glutaraldehyde solution at room temperature for at least 3 hours (14). As is well known, glutaraldehyde effects cross-linking of the proteins, e.g., collagen, within the tissue. Such cross-linking tends to make the tissue more durable and effects preservation thereof. It is known that cross-linked protein exhibits increased resistance to proteolytic cleavage and further that one of the major processes by which circulating blood may destroy tissue is via enzymatic activity which involves unfolding of the protein substrate in order to facilitate enzymatic hydrolysis. Cross-linking of the protein of a tissue makes the tissue resistant to such unfolding, and consequently tends to prevent deterioration thereof due to the enzymatic activity of blood.

The tissue is next sterilized, preferably with an alcohol/formaldehyde solution for 2 hours at room temperature (16). The preferred solution for effecting sterilization of the tissue comprises approximately 12 ml/l of Tween 80 (polyoxyethylene (20) sorbitan monooleate); approximately 2.65 gms/l of $MgCl_2.(H_2O$; approximately 108 ml/l of formaldehyde (37%); approximately 220 ml/l of ethyl alcohol (100%) and approximately 4.863 gms/l of HEPES buffer. The balance of the solution comprises double filtered $H_2O$. The pH of the solution is typically adjusted to 7.4 via the addition of NaOH. Those skilled in the art will recognize various other sterilization solutions are likewise suitable.

Antimineralization treatment (18) is optionally performed so as to inhibit the accumulation of mineral deposits upon the biological tissue after implantation of a mammalian body. As those skilled in the art will recognize, various different antimineralization treatments are utilized so as to prevent the deposition of various different minerals upon the biological tissue.

The tissue is trimmed and any non-biological components are then added thereto (20). For example, it is common to sew a heart valve to a valve holder which aids in the handling thereof and which may additionally function as a mount for the valve when implanted into a mammalian body.

Next, the biological tissue is once again sterilized (22), preferably in an alcohol/formaldehyde solution as discussed above. Since preparation of the biological tissue is substantially complete and the biological tissue will next likely be stored for an extended period of time, a more rigorous sterilization procedure from that previously utilized is typically employed. At this stage, the biological tissue is typically sterilized for approximately 9 hours at 34–38° C.

After sterilization, the biological tissue is stored in glutaraldehyde at room temperature (24).

Referring now to FIG. 2, the method for treating glutaraldehyde fixed biological tissue to inhibit calcification thereof following implantation in a mammalian body comprises the additional step of heating preferably when the glutaraldehyde is in contact with the biological tissue, to approximately 35–55° C. for approximately 4–22 weeks.

Heating of the biological tissue may be performed at any time after harvesting the tissue from the animal or human cadaver and prior to implanting the tissue within a mammalian body. However, heating of the biological tissue is preferably performed at a point in the process for preparing the biological tissue when the biological tissue is already disposed within a bath of glutaraldehyde solution, as occurs at various stages of the process according to the prior art. Thus, the method for treating glutaraldehyde fixed biological tissues according to the present invention is preferably performed either during fixing thereof with a glutaraldehyde solution, immediately after fixing thereof with the glutaraldehyde solution, or alternatively just prior to or after being stored in a glutaraldehyde solution.

As a further alternative, the method for treating glutaraldehyde fixed biological tissues may be performed during antimineralization treatment by adding glutaraldehyde to the antimineralization solution and heating the solution, preferably to approximately 35–55° C. for approximately 4–22 weeks.

For example, after fixing tissue using a 0.625% glutaraldehyde solution at room temperature for at least 3 hours (14), the biological tissue may be heat treated in either the same or different 0.625% glutaraldehyde solution, preferably at approximately 35–55° C. for approximately 4–22 weeks (15).

As one of the alternatives discussed above, the biological tissue is fixed and heat treated simultaneously (13) in the 0.625% glutaraldehyde solution, again preferably at approximately 35–55° C. for approximately 4–22 weeks. Another alternative is to heat the tissue in saline (17) prior to fixation (21).

As the other alternative discussed above, the biological tissue may simultaneously undergo antimineralization treatment and heat treatment (19). Glutaraldehyde is added to the antimineralization solution so as to effect the inhibition of calcification of the tissue following implantation in a mammalian body.

Thus, the method for treating fixed biological tissue so as to inhibit calcification thereof following implantation in a mammalian body tends to substantially increase the usable life of such tissue subsequent to implantation in a mammalian body, thereby mitigating the requirement for subsequent tissue replacement. As those skilled in the art will appreciate, such tissue replacement frequently causes substantial trauma to the patient, occasionally resulting in the patient's death. As such, it is greatly beneficial to be able to either avoid or postpone the need for the replacement of implanted biological tissue.

It is understood that the exemplary method for treating glutaraldehyde fixed biological tissue described herein and shown in the drawings represents only a presently preferred embodiment of the present invention. Indeed, various modifications and additions may be made to such embodiment without departing from the spirit and scope of the invention. For example, various fixing agents, such as aldehydes other than glutaraldehyde, may exhibit properties similar to those of glutaraldehyde so as to make them suitable for use in the present invention and, thus, may likewise be utilized. Accordingly, these and other modifications and additions may be obvious to those skilled in the art and may be implemented to adapt the present invention for use in a variety of different applications.

What is claimed is:

1. A method for treating bovine pericardium tissue or porcine tissue to inhibit calcification of the tissue following implantation in a mammalian body, the method comprising the steps of:

fixing the tissue;

after fixing, heat treating the tissue in a fixative at a temperature of between about 35–55° C. for a period of between 4–22 weeks; and sterilizing the tissue after fixing and prior to heat treating in a solution comprising an alcohol, formaldehyde and polyoxyethylene 20 sorbitan monooleate.

2. The method of claim 1, wherein the step of fixing includes placing the tissue in contact with an approximately 0.625% solution of glutaraldehyde comprising:

a) approximately 26 ml/l glutaraldehyde;

b) approximately 4.863 g/l HEPES buffer;

c) approximately 2.65 g/l $MgCl_2.6H_2O$;

d) approximately 4.71 g/l NaCl; and e) balance of solution double filtered $H_2O$;

wherein the method further includes adjusting the pH of the solution to approximately 7.4.

3. The method of claim 1, wherein the period is several months.

4. The method of claim 1, comprising the additional step of storing the tissue after sterilizing and then performing the heat treatment during storage.

5. The method of claim 1 wherein the fixative is glutaraldehyde and wherein the heat treating further includes:

placing the tissue in a glutaraldehyde-containing antimineralization solution; and heating the glutaraldehyde-containing antimineralization solution.

6. The method of claim 1 wherein the fixative is glutaraldehyde and wherein the heat treating further includes disposing the tissue in a solution of glutaraldehyde and heating the solution of glutaraldehyde.

7. The method of claim 6, wherein the period is several months.

8. The method of claim 6, wherein the solution of glutaraldehyde is an approximately 0.625% solution of glutaraldehyde comprising:

a) approximately 26 ml/l glutaraldehyde;

b) approximately 4.863 g/l HEPES buffer;

c) approximately 2.65 g/l $MgCl_2.6H_2O$;

d) approximately 4.71 g/l NaCl; and e) balance of solution double filtered $H_2O$;

wherein the method further includes adjusting the pH of the solution to approximately 7.4.

9. A method for treating biological tissue to inhibit calcification of the tissue following implantation in a mammalian body, the method comprising:

fixing the tissue in a solution comprising a fixative agent;

storing the tissue in a solution comprising a fixative agent;

heating the stored tissue in said solution to a temperature between about 35–55° C.; and prior to storing the tissue, sterilizing the tissue in a solution comprising an alcohol, formaldehyde and polyoxyethylene 20 sorbitan monooleate.

10. A method according to claim 9, wherein the tissue is heat treated in a solution selected from the group consisting of a physiologic solution and a glutaraldehyde solution.

11. A method according to claim 9, wherein the step of heating the stored tissue is carried out for a period of time in the range of about a few seconds to 22 weeks.

12. A method according to claim 11, wherein the step of heating the stored tissues is carried out for a period of time in the range of about 4 to 22 weeks.

13. A method for treating biological tissue to inhibit calcification of the tissue following implantation in a mammalian body, the method comprising:

heat treating the tissue;

sterilizing the tissue separately from the heat treating step by contacting the tissue with a solution comprising an alcohol, formaldehyde and polyoxyethylene 20 sorbitan monooleate; and fixing the tissue in a solution comprising a fixative agent.

14. A method according to claim 13, wherein the tissue is heat treated in a solution selected from the group consisting of a physiologic solution and a glutaraldehyde solution.

15. A method according to claim 13, wherein the step of heating the stored tissue is carried out for a period of time in the range of about a few seconds to 22 weeks.

16. A method according to claim 15, wherein the step of heating the stored tissues is carried out for a period of time in the range of about 4 to 22 weeks.

17. A method according to claim 13, wherein the tissue is heat treated at a temperature in the range of about 35–55° C.

18. A method for treating biological tissue to inhibit calcification of the tissue following implantation in a mammalian body, the method comprising:

heat treating the tissue prior to implantation;

fixing the tissue in a solution comprising a fixative agent during the heat treating step; and sterilizing the tissue in a solution comprising an alcohol, formaldehyde and polyoxyethylene 20 sorbitan monooleate, storing the tissue, and wherein the heat treating is performing during storage.

19. A method according to claim 18, wherein the tissue is heat treated in a solution selected from the group consisting of a physiologic solution and a glutaraldehyde solution.

20. A method according to claim 18, wherein the step of heating the stored tissue is carried out for a period of time in the range of about a few seconds to 22 weeks.

21. A method according to claim 20, wherein the step of heating the stored tissues is carried out for a period of time in the range of about 4 to 22 weeks.

22. A method according to claim 21, wherein the period is several months.

23. A method according to claim 21, wherein the tissue is heat treated at a temperature in the range of about 35–55° C.

24. A method according to claim 18, wherein the tissue is heat treated at a temperature in the range of about 35–55° C.

25. A method according to claim 18, wherein the tissue is fresh prior to heat treating.

26. A method according to claim 18, wherein the tissue is fixed prior to heat treating.

27. A method according to claim 18, wherein the heat treating further includes disposing the tissue in a solution of glutaraldehyde and heating the solution of glutaraldehyde.

28. The method of claim 27, wherein the solution of glutaraldehyde comprises an approximately 0.625% solution of glutaraldehyde comprising:

a) approximately 26 ml/l glutaraldehyde;

b) approximately 4.863 g/l HEPES buffer;

c) approximately 2.65 g/l $MgCl_2.6H_2O$;

d) approximately 4.71 g/l NaCl; and e) balance of solution double filtered $H_2O$;

wherein the method further includes adjusting the pH of the solution to approximately 7.4.

29. A method according to claim 18, wherein the heat treating further includes:

placing the tissue in a glutaraldehyde-containing antimineralization solution; and heating the glutaraldehyde-containing antimineralization solution.

* * * * *